United States Patent [19]

Amis et al.

[11] 4,242,758
[45] Jan. 6, 1981

[54] ELBOW PROSTHESIS

[75] Inventors: Andrew A. Amis, Leeds, England; James H. Miller, Glasgow, Scotland

[73] Assignee: University of Leeds Industrial Service Ltd., United Kingdom

[21] Appl. No.: 911,031

[22] Filed: May 30, 1978

[30] Foreign Application Priority Data

Jun. 1, 1977 [GB] United Kingdom .............. 23129/77

[51] Int. Cl.³ .............................................. A61F 1/03
[52] U.S. Cl. ..................................... 3/1.91; 128/92 C
[58] Field of Search ........................ 3/1.9, 1.91, 1.911; 128/92 C

[56] References Cited

U.S. PATENT DOCUMENTS

| 3,547,115 | 12/1970 | Stevens | 3/1.91 X |
| 3,852,831 | 12/1974 | Dee | 128/92 CX |
| 3,919,725 | 11/1975 | Swanson et al. | 128/92 CX |
| 4,038,704 | 8/1977 | Ring | 3/1.91 |
| 4,057,858 | 11/1977 | Helfet | 3/1.91 |
| 4,073,999 | 2/1978 | Bryan et al. | 3/1.9 X |
| 4,079,469 | 3/1978 | Wadsworth | 128/92 CX |

FOREIGN PATENT DOCUMENTS 1444724  8/1976  United Kingdom ....................... 3/1.91

*Primary Examiner*—Clifford D. Crowder
*Attorney, Agent, or Firm*—Stevens, Davis, Miller & Mosher

[57] ABSTRACT

An elbow prosthesis having a humeral component having spherical, articular surface portions which together extend over substantially the whole of the length of the component and which are shaped and dimensioned for improved fit with the ulna and radius or with prosthetic components located thereon. The invention also provides a set of instruments suitable for shaping the end of a bone to receive a prosthetic component.

19 Claims, 31 Drawing Figures

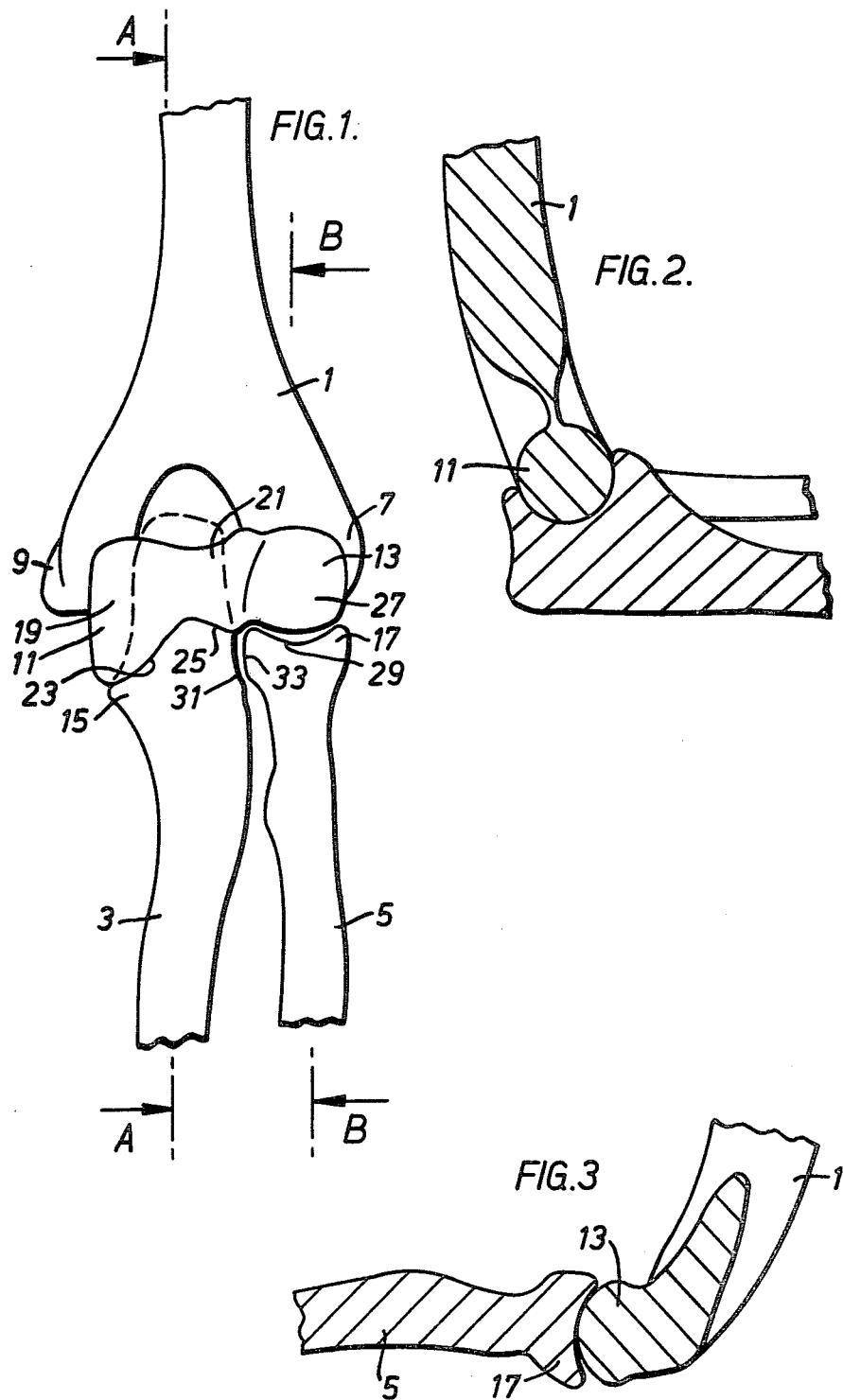

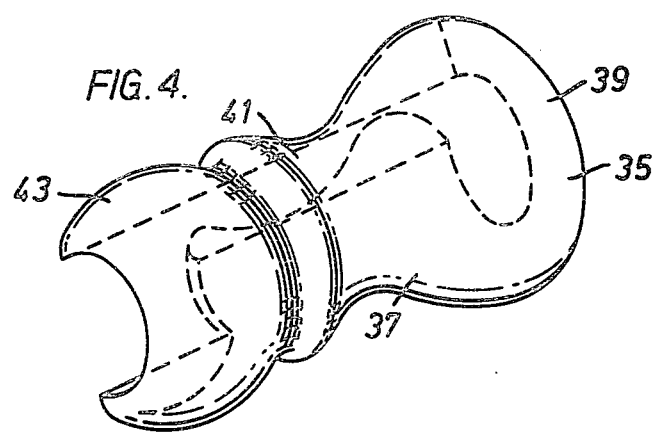
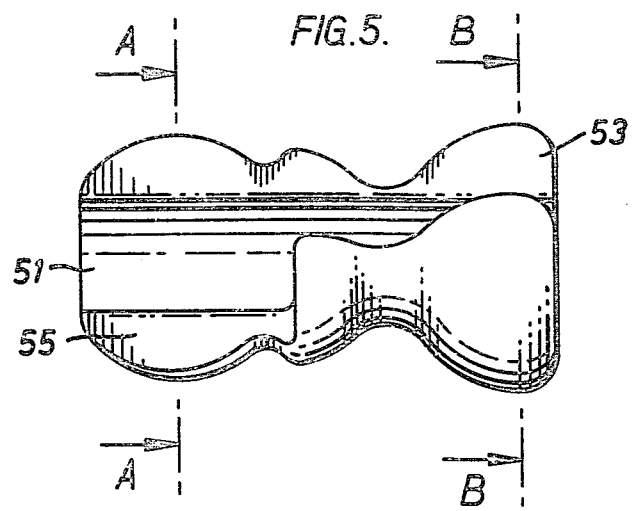
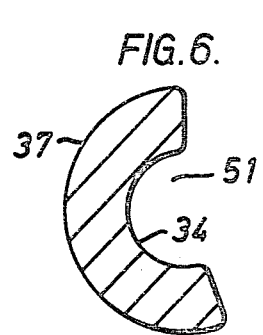 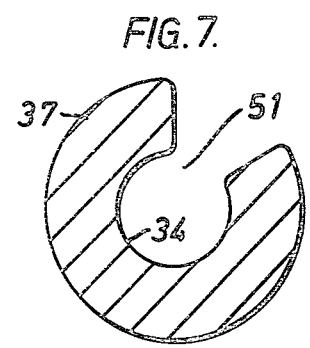

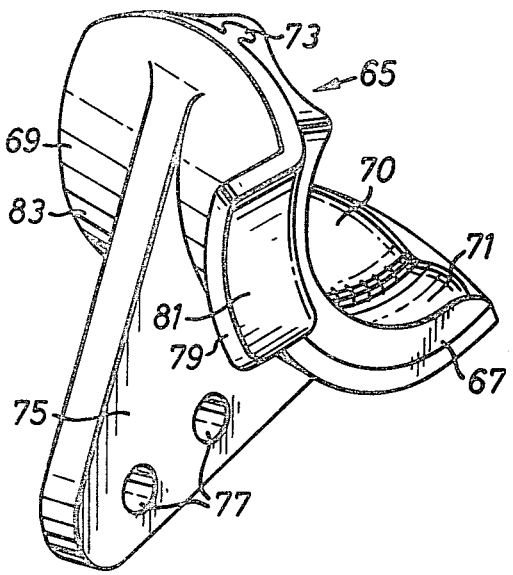
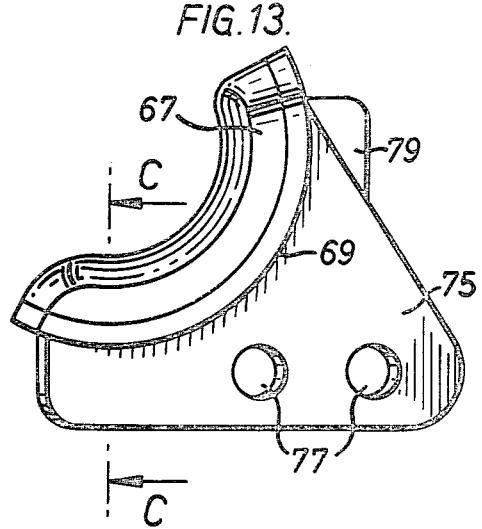
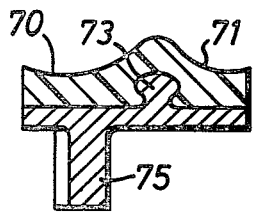
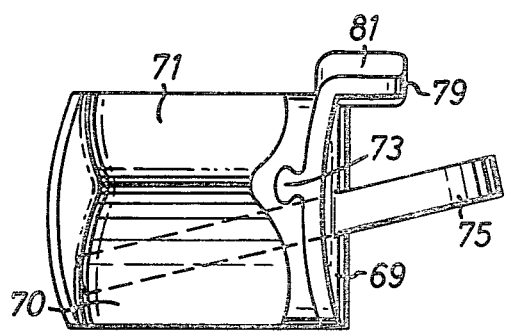

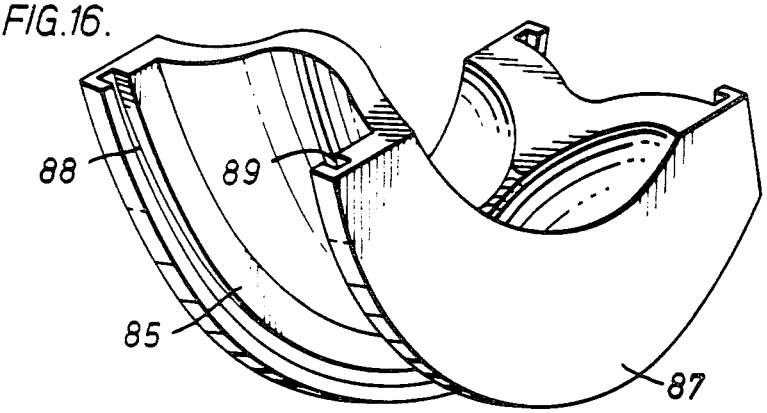
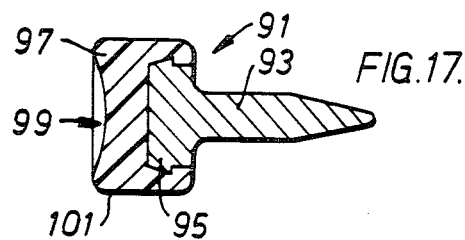
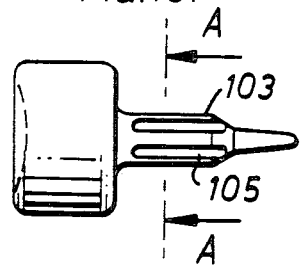
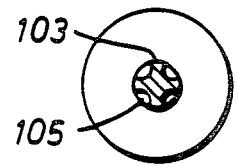
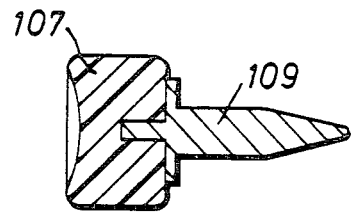

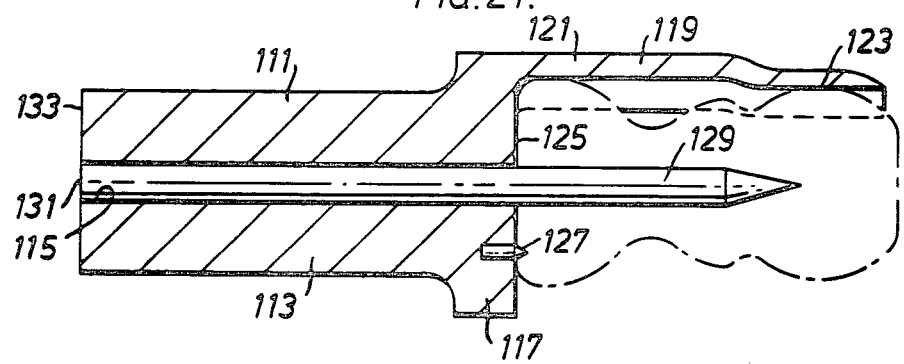
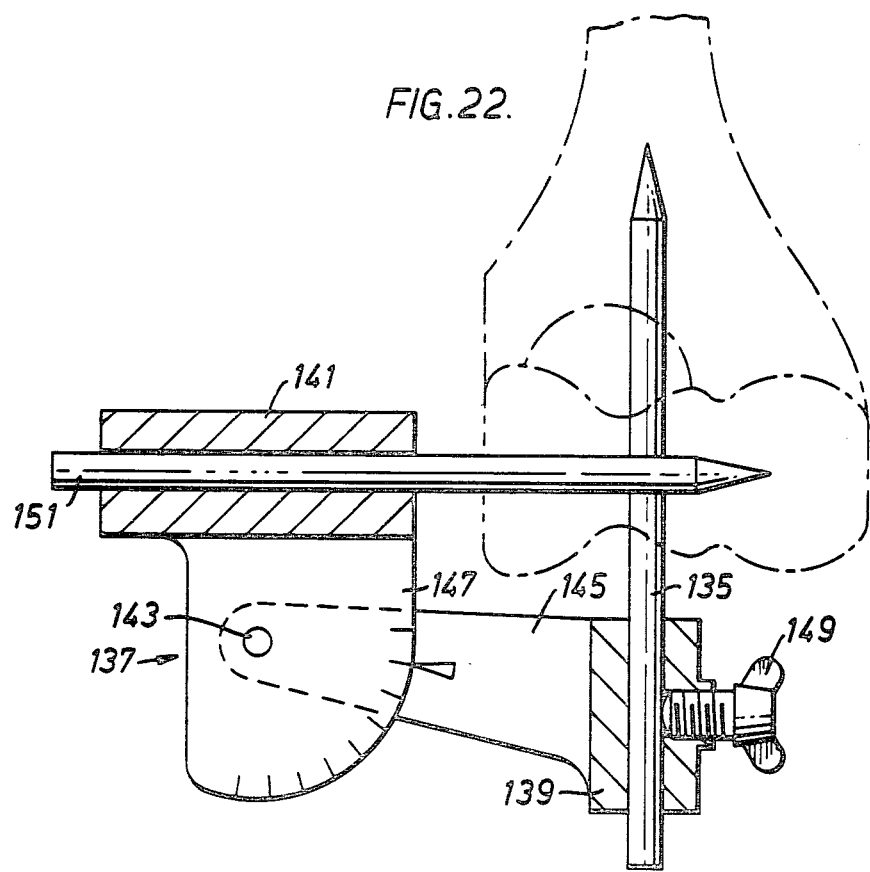

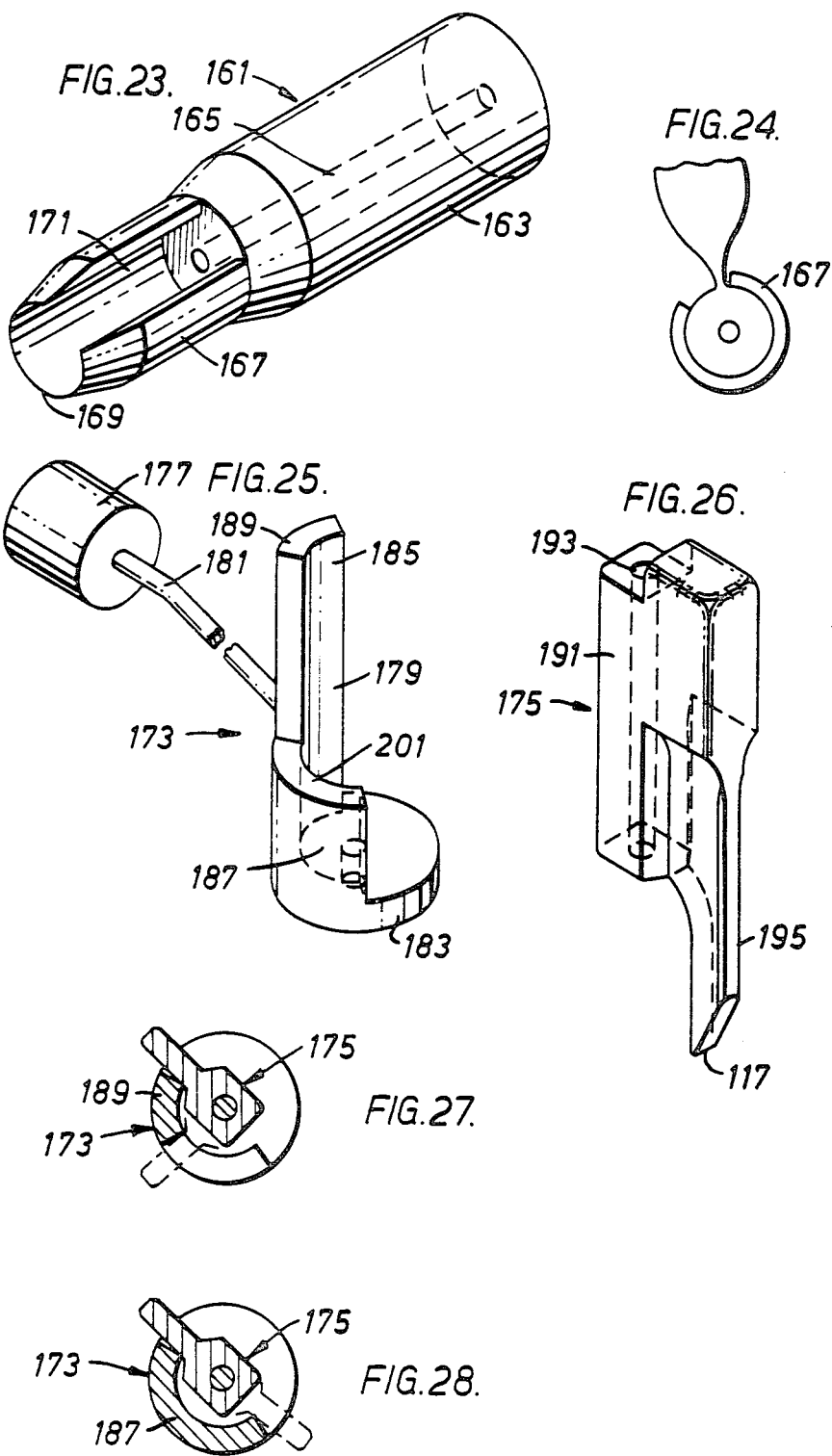

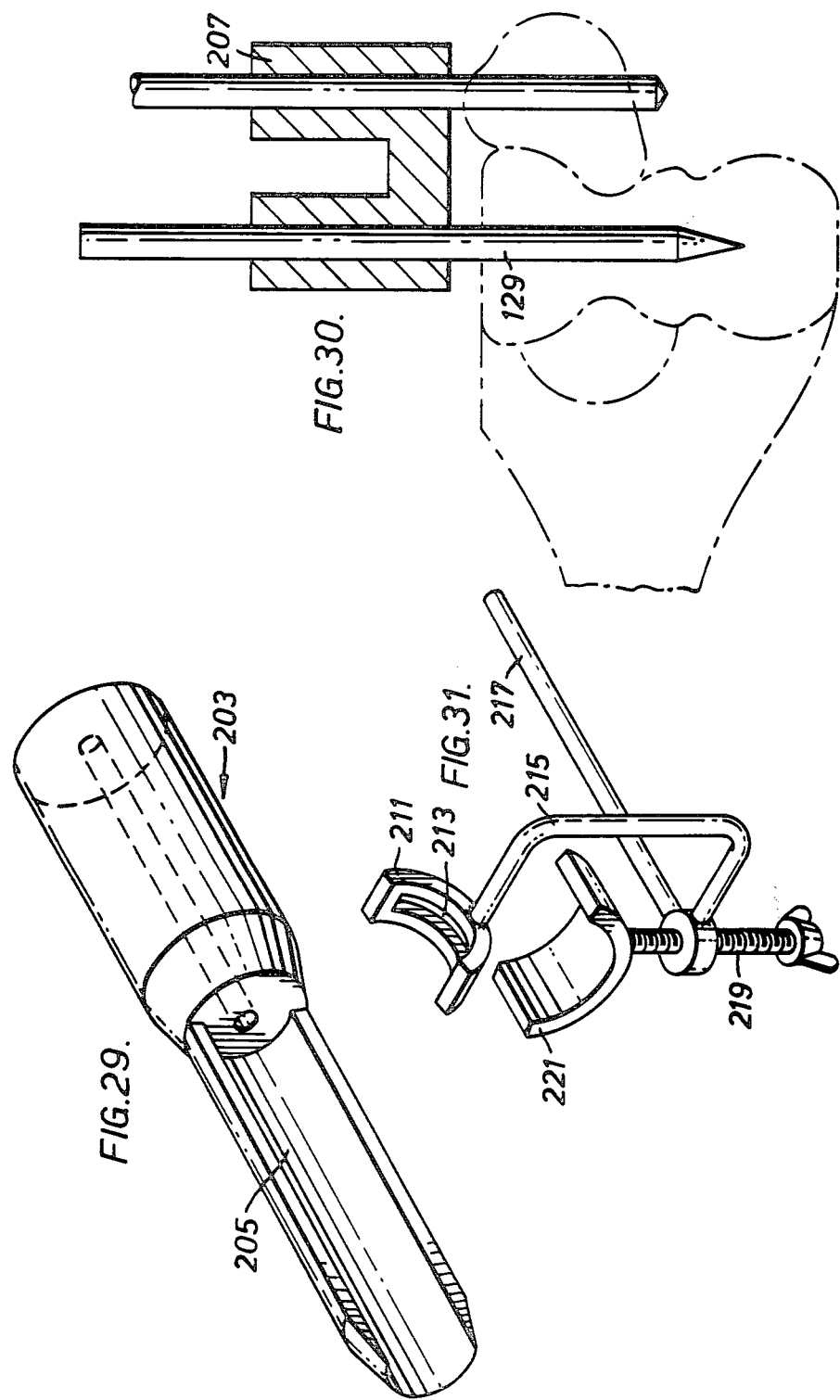

ELBOW PROSTHESIS

This invention relates to an elbow prosthesis.

Elbow prostheses are known which comprise simple hinge arrangements, one component of which is attached to the end of the humerus and the other component of which is attached to the end of the ulna. The humeral component includes a shaft which is cemented into a reamed out bore in the end of the humerus and the ulnar component includes a shaft which is cemented to the end of the ulna. The head of the radius is removed and the components of the prosthesis are connected together by means of a hinge pin so that the prosthesis allows a single degree of freedom of movement of the ulna relative to the humerus. A large amount of bone is removed in order to insert such a prosthesis. Furthermore, since during use of the arm forces are transmitted up the radius, these forces have the effect of loosening the prosthesis and, often only a year or two after insertion of the prosthesis, cause pain at the wrist.

Elbow prostheses are also known which have the advantage over the above-mentioned prostheses that the components are in effect surface or onlay replacements which cap the end of the bones and involve much less destruction of the bones. The humeral component is bobbin-shaped and fits over the trochlea which during the operation is shaped to accommodate this component. The ulnar component is provided with a concave surface for sliding engagement with the humeral component so such a prosthesis still only allows a single degree of freedom of movement at the elbow joint. The head of the radius is again removed and therefore a prosthesis of this type still suffers the same disadvantage with regard to the forces transmitted through the radius. Such prostheses have been designed so that the contact between the humeral and ulnar components is slack, thereby allowing a sideways movement of the ulna and radius relative to the humerus of about ten degrees from the longitudinal axis. However, by arranging such a slack fit there is then only line contact between the components and the resultant high pressures cause rapid wear on one or both of the components. Furthermore, if, in use, the surrounding ligaments do not tighten before the limit of the sideways movement, the forces are transmitted entirely through the components of the prosthesis.

Recently a prosthesis of the onlay type has been proposed in which the humeral component extends across the whole of the width of the trochlea and capitellum. This prosthesis, known as the ICLH prosthesis, therefore has a much wider humeral component than those of earlier designs and, since it extends over the whole of the end of the bone, will both resist torsional loading and spread compression loads over a wide area. The region of the humeral component which is located over the trochlea has a substantial cylindrical articulating surface and the ulnar component has a corresponding concave surface for sliding movement about the cylindrical surface of the humeral component. It is believed that the portion of the humeral component which is located over the capitellum may be shaped to engage a third component of the prosthesis which replaces the radial head so that there can be sliding movement therebetween.

Finally, an elbow prosthesis is now known which consists of a single component designed to replace the end of the humerus and arranged for sliding contact against the heads of both the radius and the ulna. This prosthesis, known as the Street-Stevens prosthesis, is an essentially tubular shaped component with a longitudinal slot extending the entire length of the component. In order to insert such a prosthesis, the ends of the trochlea and capitellum are trimmed to produce a narrow tongue across the full width of the trochlea and capitellum. The prosthesis is then fitted over the end of this tongue.

The outer surface of the Street-Stevens prosthesis is provided with a bobbin shaped portion for locating the ulna and a spherical portion for locating the radial head.

It has now been discovered that the relative dimensions of the portions of the outer surface of a humeral prosthesis of the type which extends across the full width of the trochlea and capitellum are of great importance.

According to a first aspect of the present invention, there is provided an elbow prosthesis comprising a humeral component for fitting over the end of the humerus to provide surfaces replacing the natural articulating surfaces of the trochlea and capitellum, the component being an elongate member of substantially C-cross section, the inner surface of which is for engagement with the end of the humerus and the outer surface of which is provided with first, second and third spherical surface portions, the first and third spherical surface portions being arranged on either side of the second spherical surface portion and the three spherical surface portions together extending over substantially the whole of the length of the component, the first and second spherical surface portions being for engagement with the ulna or a prosthetic component located thereon and the third spherical surface portion being optionally for engagement with the radius or a prosthetic component located thereon, the diameter of the first spherical surface portion being greater than the diameter of the third spherical surface portion and the ratio of the distance from the lateral end of the humeral component to the position of maximum diameter of the humeral component in the region of the second spherical surface portion to the length of the humeral component being less than 0.5.

A humeral prosthesis in accordance with the present invention has an outer surface which closely resembles that of the natural trochlea and capitellum.

Preferably at the ratio of the diameter of the first spherical surface portion to the diameter of the third spherical surface portion is from 1.1 to 1.3 and more preferably is about 1.2.

Preferably the ratio of the length of the humeral component to the distance from the lateral end of the humeral component to the position of maximum diameter of the humeral component in the region of the second spherical surface portion is from 0.45 to 0.49 and more preferably about 0.47. In the Street-Stevens prosthesis this ratio is about 0.55 and it is found that the smaller value for this ratio in the prosthesis of the present invention enables a much better fit of the prosthesis with artificial or natural components on the ulna and radius.

In a second aspect the present invention provides an elbow prosthesis comprising a humeral component for fitting over the end of the humerus to provide surfaces to replace the natural articulating surfaces of the trochlea and capitellum, the component being an elongate member of substantially C-shaped cross-section, the inner surface of which is for engagement with the end of the humerus and the outer surface of which is provided with first, second and third spherical surface portions, the first and third spherical surface portions being arranged on either side of the second spherical surface portion and the three spherical surface portions together extending over substantially the whole of the length of the component, the first and second spherical surface portions being for engagement with the ulna or a prosthetic component located thereon and the third spherical surface portion being optionally for engagement with the radius or a prosthetic component located thereon, the arcuate extent of the humeral component, for that region which includes the first and second spherical surface portions, being such that the angle subtended in a plane at right angles to the longitudinal axis of the humeral component is from 270 degrees to 315 degrees and for the region of the third spherical surface portion is from 190 degrees to 210 degrees.

Preferably the first above-mentioned angle is about 300 degrees and the second above-mentioned angle is about 200 degrees.

These angles correspond closely to the angles subtended by the natural articular surfaces so the prosthesis covers those areas of bone which were previously covered by articular cartilage.

A prosthesis in accordance with the above-mentioned first aspect of the present invention comprises a humeral component whose arcuate extent, for that region which includes the first and second spherical surface portions, is, as with a prosthesis in accordance with the second aspect of the present invention, such that the angle subtended in a plane at right angles to the longitudinal axis of the humeral component is from 270 degrees to 315 degrees and for the region of the third spherical surface portion is from 190 degrees to 210 degrees. Alternatively the arcuate extent of the humeral component is constant over substantially the whole of the length of the humeral component and preferably from 210 to 270 degrees.

In order to insert the prosthesis the trochlea and capitellum are trimmed to a shape to match the inner surface of the prosthesis so that, preferably, there is an interference fit between the bone and the prosthesis. The bone enters the prosthesis through the variable opening extending the entire length of the prosthesis and since this opening is relatively large there is considerable support for the end of the humerus and the prosthesis. Furthermore, the opening in the region of the capitellum is preferably relatively very wide and the blood supply to the capitellum can enter the bone behind the capitellum thereby minimizing the danger that the blood supply may be cut off and the bone within the prosthesis die as a result thereof.

Preferably an elbow prosthesis in accordance with the present invention includes an ulnar component which is designed to fit against the trochlear surfaces of the humeral component. Preferably the ulnar component is in the form of a cap for fitting on the end of the ulna, the ulna having been shaped to accommodate this cap, and the cap having a concave articulating surface for sliding contact with the humeral component. The ulnar component may be provided with an integral fixation plate which is shaped to fit within the proximal medullary cavity of the ulna. In an alternative embodiment the ulnar component is provided with a pair of fixation flanges for fitting alongside the ulna from the coronoid process to the olecranon process.

A further alternative ulnar component may be provided with a pair of fixation flanges for fitting on either side of the olecranon process and a stem for location within the coronoid process.

More preferably the ulnar component is provided with two spherical concave surface portions which match the first and second spherical surface portions of the humeral component. Preferably the articulating surface of the ulnar component subtends an angle of about 150 degrees.

Preferably an elbow prosthesis in accordance with the present invention also includes a radial component which replaces at least a portion of the head of the radius and has an articulating surface shaped to engage the third surface of the humeral component. Preferably the radial component includes a substantially cylindrical head portion, one end of which is provided with a shallow concave spherical surface for engagement with the third surface of the humeral component and from the other side of which extends a stem member for location within the radius.

Preferably the humeral component is made of metal. More preferably the inner surface of the humeral component is provided with hollows which have been either cast or machined in the surface and which are filled with a porous metal layer. This porous metal layer is produced by a sintering process and the resultant layer is such that it promotes growth of bone into the layer which aids the fixation of the component to the bone. The sintered metal of this layer is produced from a powder of the same metal alloy as the rest of the component. The process for producing such a porous metal layer has been described by Canox of Bellville, Ontario, Canada whose U.K. subsidiary is Deloro-Surgical.

The ulnar component may be an integral plastics structure which is secured to the ulna by means of bone cement. Alternatively the ulnar component may comprise a plastics liner which is provided with the articulating surface and which is secured to a metal outer shell. The metal portion, which will contact at the bone of the ulna may be provided with a porous metal layer, similar to that described above in connection with the humeral component.

Preferably the humeral and ulnar components are shaped to allow for some degree of lateral rotation therebetween. By the provision of two spherical surfaces on the ulnar component which mate with the corresponding first and second surface portions of the humeral component, lateral rotation is possible between a position where only one of the spherical surfaces of the ulnar component is in contact with the corresponding surface portion of the humeral component to a position in which only the other of the spherical surfaces of the ulnar component is in contact with the corresponding surface portion of the humeral component. However, even at these two extreme positions the contact between the ulnar and humeral components is a surface contact rather than merely a point or line contact between components and therefore high stresses between these components are avoided.

In a third aspect the present invention provides a set of instruments for enabling the end of a bone, such as the trochlea and capitellum of the humerus, to be shaped, comprising guide means including an elongate member having a bore therethrough and means for aligning the elongate member so that the bore lies in a particular orientation relative to the end of the bone, a pin for locating within said bore so as to be driven into the bone along the axis of the bore, and bone shaping means adapted for location on the pin, and provided with cutting edges or the like for shaping the end of the bone.

A set of instruments in accordance with the invention is particularly useful for shaping the end of a bone to be an interference fit with a prosthesis such as the humeral component of the prosthesis of the invention. Thus the end of the bone can be accurately shaped since the shaping components are all located on the pin for sliding movement relative thereto, and the bone may therefore be trimmed very accurately about the axis of the pin. This accurate shaping of the bone is particularly useful where the prosthesis is provided with a porous metal layer into which the bone is intended to grow. Thus to be effective it is highly desirable that there should be a very close fit between the bone and the surface of the prosthesis.

Preferably the elongate member of the guide means has, extending from one end thereof, bone surface conforming means shaped so that when said conforming means is in contact with at least two positions at the end of the bone, the bore within said elongate member is aligned along a particular axis relative to the bone.

The set of instruments in accordance with the present invention may include cutting members and chisels which are each provided with an elongate portion having a bore therethrough so that they may be located on the pin to ensure accurate trimming of the bone.

Embodiments of the present invention will now be described by way of example only and with reference to the accompanying drawings, in which:

FIG. 1 shows the bones of a natural elbow joint;

FIG. 2 is a section on the line A—A of FIG. 1;

FIG. 3 is a section on the line B—B of FIG. 1;

FIG. 4 is a perspective view of a humeral component of a right side prosthesis in accordance with the present invention;

FIG. 5 is a view, from the posterior aspect, of the humeral component of a left side prosthesis in accordance wih the present invention;

FIG. 6 is a section on the line A—A of FIG. 5;

FIG. 7 is a section on the line B—B of FIG. 5;

FIG. 12 is a perspective view of an ulnar component of a prosthesis in accordance with the present invention;

FIG. 13 is a side view of the ulnar component of FIG. 12;

FIG. 14 is a section on the line C—C of FIG. 13;

FIG. 15 is a top view of the ulnar component shown in FIG. 13;

FIG. 16 is a perspective view of an alternative ulnar component of a prosthesis in accordance with the present invention;

FIG. 17 is a longitudinal section through a radial component for a prosthesis in accordance with the present invention;

FIG. 18 is a side view of an alternative radial component for a prosthesis in accordance with the present invention;

FIG. 19 is a view on the line A—A of FIG. 17;

FIG. 20 is a section of a further alternative radial component for a prosthesis in accordance with the present invention; and FIGS. 21 to 31 illustrate the operating procedure and instruments associated therewith for inserting a prosthesis in accordance with the present invention.

Figure 8:
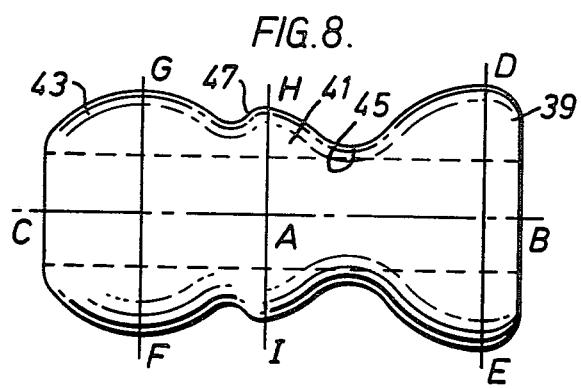
FIG. 8 is a front view of the humeral components of FIG. 4.
Figure 9:
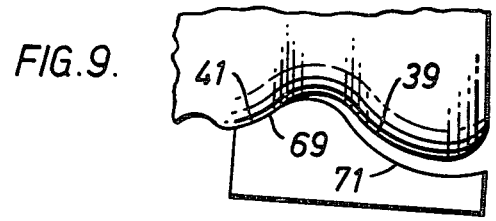
FIGS. 9 and 10 illustrate the lateral rotation of humeral and ulnar components of the prosthesis according to the present invention.
Figure 10:
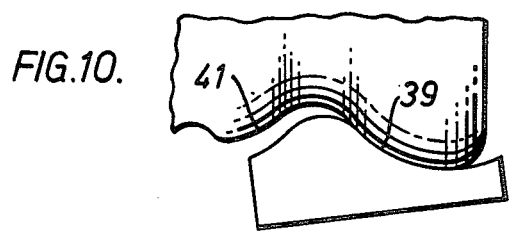
Figure 11:
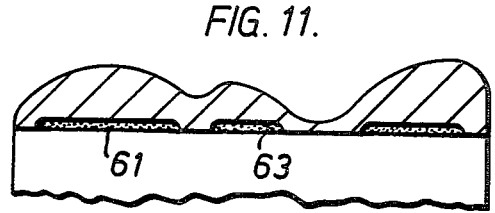
FIG. 11 is a longitudinal section of a humeral component in accordance with the present invention.

Referring to FIGS. 1 to 3 of the drawings, the bones of the arm comprise the humerus 1, the ulna 3 and the radius 5. At the elbow the humerus widens to its lateral and medial epicondyles 7 and 9 and is provided at its end with articulating surfaces on the trochlea 11 and the capitellum 13. These articulating surfaces engage with corresponding surfaces on the coronoid process 15 of the ulna 3 and the head 17 of the radius 5. It can be seen that the trochlea is provided with two curved articulating surfaces 19 and 21 which engage with corresponding articulating surfaces 23 and 25 of the ulna. The capitellum 13 is provided with a single articulating surface 27 which engages a corresponding surface 29 of the head 17 of radius 5. Ulna 3 and radius 5 are each provided with surfaces 31 and 33 which engage with each other.

Referring now to FIGS. 4 to 11, it can be seen that a humeral component 35 is an elongate member of substantially C-shaped cross section, inner surface 34 of which is for engagement with the end of the humerus, after the latter has been trimmed to match the inner shape of the humeral component. The outer surface 37 of humeral component 35 is provided with three spherical surface portions 39, 41 and 43. Surface portions 39 and 41 replace the surfaces of the natural trochlea and surface portion 43 replaces the surface of the natural capitellum and it can be seen that the outer surface of the humeral component bears a close resemblance to the surface of the natural trochlea and capitellum.

Referring particularly to FIG. 8 it can be seen that the maximum diameter of the component is at the region of spherical surface portion 39 and close to the medial end of the component. The narrowest diameter of the component occurs between surface portions 39 and 41 where there is a smooth curved portion 45 linking surface portions 39 and 41. Surface portion 41 reaches its own maximum diameter at a point A on the longitudinal axis of the component and there is between surface portions 41 and 43 a short surface portion 47 which extends relatively steeply inwardly towards the longitudinal axis of the component before meeting surface 43 in a smooth curve. Surface portion 43 extends from portion 47 to the lateral edge of the component.

The dimensions of the humeral component are such that the maximum diameter HI of the surface portion 41 is slightly less than maximum diameter FG of surface portion 43. Furthermore the maximum diameter DE of surface portion 39 is significantly greater than maximum diameter FG. This again reproduces the dimensions of the natural trochlea and capitellum.

The ratio of the distance AC between the lateral end of the component and the position of maximum diameter of surface portion 41, to BC, the total length of the prosthesis, is about 0.47 which again is close to the average for this ratio for the average natural trochlea and capitellum.

Referring in particular to FIGS. 4 to 7 it can be seen that the humeral component is in the form of a tube having a constant diameter inner surface, the wall of the tube having a cut out portion 51 extending the entire length of the component. One edge 53 of cut out portion 51 is flat whereas the other edge 55 is stepped at surface portion 47 so that the gap between edges 53 and 55 is substantially larger across surface portion 43 than across surface portions 39 and 41. The result is that surface portion 43 subtends an angle of about 200° whereas surface portions 39 and 41 subtend an angle of about 300°. These angles are similar to those of the natural capitellum and trochlea and accordingly the articulating surfaces of the humeral component replace only those areas of bone previously covered by articular cartilage.

In an alternative embodiment (not illustrated) the angle subtended by the surface portions of the humeral component is constant over the whole of the length of the component and preferably is intermediate between the angles subtended by surface portion 43 on the one hand and surface portions 39 and 41 on the other hand of the above-described component.

The humeral component is made of metal and may for instance be of stainless steel such as EN 58J. Preferably however the humeral component is made from a cobalt chrome alloy such as VITALLIUM or a titanium alloy such as in BS3531. Alloys such as these are particularly suitable to receive a layer or layers of sintered-in porous metal 61 which may be applied to hollows 63 let into the inner surface of the component. Alternatively the humeral component could be intended for location purely by means of cement. In this case the design would be very similar, except that the inner surface would be left at a plane cylindrical surface, albeit with this surface being roughened to aid fixation to the cement and bone.

Referring to FIGS. 12 to 15 the ulnar component 65 of a prosthesis in accordance with the present invention comprises a plastics liner 67 attached to a metal support 69. The angle subtended by plastics liner 67 in the plane of FIG. 13 is about 150° and the plastics bearing surface is provided with two concave portions 70 and 71 which are separated by a rigid 73. These surface portions 70, 71 match surface portions 39 and 41 respectively of the humeral components. Thus the bearing surface of the ulnar component follows closely the bearing surface of the coronoid process of the natural ulna. However the ulnar component of the prosthesis differs from the natural ulna in that at its proximal end the plastics liner does not extend as far as the natural bearing surface so as to allow the humeral component to guide into slight dislocation during transverse (or lateral) rotational movements. By omitting the natural central posterior ridge, one avoids the build up of loosening torques which might otherwise shorten the lifetime of the prosthesis.

Metal support 69 is attached to plastics liner 67 by means of a simple mechanical detent fixation provided by an integral tongue 73 locating within a matching groove within the plastics liner.

Metal support 69 is provided with an integral fixation plate 75 which is shaped to fit within the proximal medullary cavity of the ulna. As can best be seen in FIG. 15 it is arranged at an angle of about 13° to the transverse axis of the component so as to be able to follow the above mentioned cavity of the ulna. Fixation plate 75 is provided with holes 77 to aid fixation within the bone. On the lateral side of ulnar component 65 and integral with metal support 69 there is provided lateral extension member 79 which is provided with a concave cylindrical bearing surface 81 which, when the component is inserted, is positioned on the ulnar side of the superior radio-ulnar joint and locates the side of the radial head component to be described below. This bearing surface therefore performs the function of surface 31 of the natural ulna, as illustrated in FIG. 1.

The fixation plate 75 and also the free surface 83 of metal support 69 is covered by a porous metal coating, as described above to aid bone ingrowth fixation.

The above described ulnar component differs from most known ulnar components in that the free surface of metal support 69 is cylindrical. Most known designs use a square-shaped component so that, in the operation procedure, the bone may be easily sawn with two straight cuts. The provision of a cylindrical surface means that there are no undue stresses at the junction of two straight cuts.

The plastics liner is made of ultra high molecular weight polyethylene and metal support 69 is made of cast cobalt chrome alloy.

In an alternative ulnar component, the component is made of a single piece of plastics material, the integral fixation plate being somewhat thicker than as shown in FIG. 12. Grooves may be machined in the surface of the plastics material to aid keying to the cement which would be used to fix an all plastics component in position in the bone.

A further alternative ulnar component is illustrated in FIG. 16 and in this case the central fixation plate is replaced by a pair of flanges 85 and 87, which, when the ulnar component is in position on the ulna lie in the sagittal plane and fit on either side of the ulna extending from the coronoid process to the olecranon process. These flanges 85 and 87 are provided with grooves 88 and 89. As illustrated this ulnar component is made of a single piece of plastics material and does not include a lateral extension member such as member 79 of the ulnar component shown in FIG. 12. In this case the radial head component will be contacting only the plastics material of the ulnar component and not any metal.

In a further embodiment of the ulnar component (not illustrated) the flanges of the embodiment shown in FIG. 16 are reduced in length so that, when the component is positioned on the ulna, the flanges fit on either side of the olecranon process but do not extend to the coronoid process. In addition the component is provided with a stem for location within the coronoid process.

Referring to FIG. 17 a radial head component 91 comprises a metal stem 93 with an enlarged end 95 which is a snap fit within a plastics head 97. The bearing surface 99 of plastics head 97 is shaped with a shallow concave curvature to match the curvature of surface portion 43 of the humeral component. The curvature of the cylindrical side wall 101 of plastics head 97 also matches the curvature of the bearing surface 81 of extension 79 of the ulnar component.

In an alternative embodiment of a radial head component, the component may be similar to that shown in FIG. 7 except that the head and stem portions may be formed so that they are easily separated. In this way the head portion may initially be made of metal in the case where a humeral prosthesis is not being fitted. Later if it is necessary to fit a humeral prosthesis, the metal head portion may then be replaced by a plastics head portion.

The surfaces of the metal stem may be provided with a layer of porous metal, similar to that described above. Grooves may be cast along the surface of the stem in order to resist torsion loads.

A further alternative radial head component, shown in FIGS. 18 and 19, is a one piece plastics component, for use with acrylic bone cement. The tip of the plastic stem 103 is longer than the metal stem in order to help resist sideways loadings. Flutes 105 provided in stem 103 help resist rotational forces.

A yet further alternative radial head component is shown in FIG. 20. In this case the component comprises a head portion 107 having a central cylindrical hole opening at the rear face thereof and, located in the hole is an integral spigot of stem member 109. The fit of the spigot of stem 109 within head portion 107 is such as to allow relative rotation between these components. Head portion 107 may be made of plastics material or may be made mainly of metal with an optional plastics liner providing the bearing surface. Stem member 109 is made of metal.

For a given diameter of radial head, the internal diameter of the neck of the bone varies greatly from one subject to another. It is therefore desirable to have both a narrow-stemmed radial head component as well as the normal design for each size of prosthesis.

Since the primary function of the radial head is to absorb axial loads, it requires sufficient thickness, in an axial direction, to maintain the geometry of the distal radio-ulnar joint. This is accomplished by making the thickness of the radial head component nearly equal to the largest natural size. If, as in most cases it is too thick, then it may be accommodated by trimming some length from the neck of the radius.

It should be appreciated that, although the radial head components can be omitted, as in the case of known elbow prostheses, it is in fact preferred that this component be included and the humeral and ulnar components are designed to accommodate the radial head component.

Referring now to FIGS. 21 to 31 there will now be described the operative procedure and instruments used in connection therewith for inserting an elbow prosthesis such as that described above.

The operative procedure is initiated by the so-called Boyd's approach to the posterior aspect. A skin incision is first made and then the anconeus muscle insertion and much of the supinator are stripped from the lateral aspect of the ulnar shaft. The muscles and lateral skin flap retract to reveal the posterial aspect of the radial head and neck. The medial skin flap is retracted, the ulnar nerve is identified, mobilised and retracted medially.

The head of the radius is then excised.

The medial epicondyle 9 is osteotomised in the same plane as the medial end face of the trochlea. (Pilot holes are drilled into the supracondylar ridge of the humerus to create a plane of weakness in preparation for this osteotomy.) In a case where the trochlea and capitellum are normal in shape pin guide 111 may be used. Guide 111 includes an elongate member 113 having a longitudinal bore 115 extending therethrough. Extending longitudinally from one enlarged end 117 of guide 111 and integral therewith is a curved template portion 119. Template portion 119 extends circumferentially over an angle of about 90° and includes a first longitudinal portion 121 and stepped inwardly therefrom a second longitudinally extending portion 123. Guide 111 is positioned with its end face 125 abutting the end of the trochlea, portion 121 of template 119 making contact with the maximum diameter portion of the trochlea and portion 123 of template 119 making contact with the maximum diameter region of the capitellum. Guide 111 also includes a short integral nail 127 which is embedded into the end of the trochlea and aids the alignment of guide 111.

The purpose of guide 111 is to enable an axis pin 129 to be driven into the trochlea and capitellum along the joint axis.

With guide 111 in position the axis pin 129 is hammered into the trochlea and capitellum until the end 131 of axis pin 129 is flush with the free end 133 of guide 111. Guide 111 is then removed.

Should the surfaces of the trochlea and capitellum be abnormal in shape due to previous trauma or arthritic erosions the instrument shown in FIG. 22 may be used correctly to position the axis pin. In this case a further pin 135 is first hammered into position roughly along the bone shaft axis. Then a guide member 137, having first and second tubular members 139 and 141 pivoted together at point 143 by means of arms 145 and 147, is located with tubular member 139 over pin 135. Screw 149 provided on tubular member 139 is then used to clamp tubular member 139 to pin 135. Tubular member 141 is then pivoted to the correct orientation, following which axis pin 129 is then hammered into the trochlea and capitellum. Tubular member 141 may be aligned by eye or alternatively an X-ray taken to check the orientation of pin 135 relative to the bone shaft axis.

Having correctly positioned axis pin 129 the trochlea and capitellum then have to be trimmed to the correct shape. The first stage of this procedure involves the use of tubular cutter 161 shown in FIG. 23. Tubular cutter 161 includes an elongate cylindrical portion 163 having a central longitudinal bore 165 therethrough. Extending from one end of elongate member 163 is the tubular cutting portion 167 which is provided with a cutting edge 169. Tubular portion 167 is provided with a longitudinal cut out portion 171 extending its entire length, the cut out portion 171 subtending an angle of 60°. Tubular cutter 161 is slid along axial pin 129 and impacted onto the medial end of the trochlea to give a 300° arc cut, the cutter being positioned such that one end of the cut lies vertically above the axis pin 129 (see FIG. 24) so that after the trimming operation the edge of the articular surface will be adjacent the anterior surface of the cortex of the bone shaft immediately proximal to the prosthesis. The length of tubular portion 167 of cutter 161 is such that the cut produced thereby extends over the trochlea but not into the capitellum. The cut produced by cutter 161 serves as a guide for bone trimming.

Cutter 161 is removed and the bone is then trimmed around the cut using chisel guide 173 and chisel 175. Chisel guide 173 includes a handle 177 which is connected to guide portion 179 by means of rod 181. Guide portion 179 includes a circular base 183 having a central hole therethrough for location on the axis pin 129. Extending from the peripheral edge of one side of base 183 is a part cylindrical portion 185. Portion 185 is stepped along one edge to provide a first portion 187 adjacent base 183 which is of relatively large circumferential extent and whose length is equal to the width of the capitellum and a second portion 189 of relatively narrow circumferential extent whose length is equal to the width of the trochlea.

The chisel 175 includes a body portion 191 which is a substantially flat elongate member having, extending down one side thereof a longitudinal bore 193. Extending longitudinally from one end of portion 191, the other side of this portion to bore 193, is an elongate cutting portion 195 having approximately square cross-section except at the free end where it narrows to a sharp cutting edge 197. The length of cutting portion 195 is equal to the width of the elbow joint plus the thickness of base portion 183 of chisel guide 173.

In order to operate the chisel 175 in conjunction with chisel guide 173 the latter is slid over axis pin 129 until base 183 contacts the end of the trochlea. The chisel 175 is then slid over the axis pin 129 and the capitellum is trimmed using the chisel which penetrates along the previously made cut as far as stepped portion 201 of the chisel guide and is prevented from trimming beyond the 300° arcuate extension of the cut because of the interference between the body of the chisel and portion 189 of the guide, as shown in FIG. 27. During the trimming process, the shape and diameter of the cut may be checked by means of the tubular cutter 161.

When the trochlea has been trimmed in this way a cut is then made in the capitellum by means of a second tubular cutter 203 shown in FIG. 29. Tubular cutter 203 is similar to cutter 161 except that the length of tubular cutting portion 205 is equal to the width of the elbow joint and the arcuate extension thereof is only 200°. This cutter is operated in the same way as cutter 161 and then the capitellum is trimmed using chisel guide 173 and chisel 175. In this case portion 187 of chisel guide 173 prevents the chisel from operating beyond the 200° cut which has been made (see FIG. 28).

In order to see whether the trochlea and capitellum have been trimmed to the correct size and shape, a mock prosthesis is fitted over these parts. This mock prosthesis is of the same internal shape as the real one, except that the internal diameter is slightly greater so as not to be an interference fit on the trimmed bone.

In fact before trimming the trochlea and capitellum the first stage of the shaping of the ulna is completed. A rigid drill guide 207 having parallel bores therethrough is located over axis pin 129. The second bore of drill guide 207 is used in order to drill a series of holes across the width of the ulna along a circular path. Following this the above-described procedure for shaping the trochlea and the capitellum is carried out. Then a chisel is used to join up the holes which have been drilled in the ulna so that bone can be removed to leave a rough cylindrical shape in the end of the ulna. This is smoothed out by a rasp to enable the ulnar component to fit closely.

In order to produce a slot in the ulna to accommodate the fixation plate of the ulnar component a device such as that shown in FIG. 31 may be used. This device includes a mock prosthesis 211 which has a curved surface for fitting the shaped surface of the ulna and is provided with a slot 213 therefor for use as a guide for a saw used for making the slot in the ulna to receive the fixation plates of the ulnar component. Mock prosthesis 211 is provided at one end of a clamp 215, the latter having extending therefrom guide bar 217 which may be laid along the bone axis to check the alignment of the mock prosthesis. Clamp 215 is also provided with screw member 219 having a curved end portion 221 which may be screwed into contact with the posterior aspect of the ulna forcing mock prosthesis 211 into position on the ulna.

Having produced a slot in the ulna to accommodate the fixation plate, the actual ulnar component may be positioned on the ulna. If the mock prosthesis 211 is removable from clamp 215 then the device shown in FIG. 31 could also be used for driving the ulnar component into position.

In order to fit the ulnar component illustrated in FIG. 16 it is not necessary to excavate a slot within the bone to accommodate a fixation plate. Once the ulna has been shaped to locate the ulnar component, cement is applied to the ulna and the component is pressed down on the cement, the grooves 88 and 89 assisting keying to the cement.

Where the ulnar component has shorter flanges and a stem as described above then the method of fixation of the component is similar to that described above although additionally it is necessary to excavate within the coronoid process to a sufficient extent to enable the stem to be located therein. However, the amount of excavation is still less than that required with the first-described embodiment having a fixation plate. Furthermore the flanges of this embodiment do not interfere with the insertions of the ligaments whereas the longer flanges of the embodiment illustrated in FIG. 16 would interfere at least to some extent.

The shaft of the radius is then reamed out so as to accommodate the stem of the radial head.

The various components are then inserted in position, with either force fits or by using cement, depending on the nature of the components, as described above. The order of insertion is the radial head component, the ulnar component and finally the humeral component.

The medial epicondyle is then reattached using a bone screw and finally the wound is closed in the usual way.

It will be appreciated that the use of axis pin 129 as a guide for all the other instruments used in the operation means that the bone can be trimmed very accurately which is particularly advantageous in the case where it is desired to force fit the humeral component over the trimmed bone.

It will also be appreciated that the above-described operative procedure does not involve anything like the complete removal of the trochea and capitellum as was required with many known prostheses. On the contrary these bone parts are merely smoothed off to enable the humeral component to be pushed over them.

We claim:

1. An elbow prosthesis comprising a humeral component for fitting over the end of the humerus to provide the entire bearing surface for the humerus by replacing the natural articulating surfaces of the trochlea and capitellum, the component being an elongate member of substantially C-cross section, the inner surface of which is for engagement with the end of the humerus and the outer surface of which is provided with first, second and third spherical surface portions, the first and third spherical surface portions being arranged on either side of the second spherical surface portion and the three spherical surface portions together extending over substantially the whole of the length of the component, the first and second spherical surface portions being for engagement with the ulna or a prosthetic component located thereon and the third spherical surface portion being optionally for engagement with the radius or a prosthetic component located thereon, the diameter of the first spherical surface portion being greater than the diameter of the third spherical surface portion and the ratio of the distance from the lateral end of the humeral component to the position of maximum diameter of the humeral component in the region of the second spherical surface portion to the length of the humeral component being less than 0.5.

2. A prosthesis according to claim 1 wherein the ratio of the diameter of the first spherical surface portion to the diameter of the third spherical surface portion is from 1.1 to 1.3.

3. A prosthesis according to claim 1 wherein the ratio of the diameter of the first spherical surface portion to the diameter of the third spherical surface portion is about 1.2.

4. A prosthesis according to claim 1 wherein the ratio of the distance from the lateral end of the humeral component to the position of maximum diameter of the humeral component in the region of the second spherical surface portion to the length of the humeral component is from 0.45 to 0.49.

5. A prosthesis according to claim 1 wherein the ratio of the distance from the lateral end of the humeral component to the position of maximum diameter of the humeral component in the region of the second spherical surface portion to the length of the humeral component is about 0.47.

6. A prosthesis according to claim 1 wherein the arcuate extent of the first-mentioned prosthesis, for that region which includes the first and second spherical surface portions, is such that the angle subtended in a plane at right angles to the longitudinal axis of the humeral component is from 270 degrees to 315 degrees and for the region of the third spherical surface portion is from 190 degrees to 210 degrees.

7. A prosthesis according to claim 6 wherein said first-mentioned angle is about 300 degrees and said second-mentioned angle is about 200 degrees.

8. A prosthesis according to claim 1 wherein the arcuate extent of the humeral component is constant over substantially the whole of the length of the component.

9. A prosthesis according to claim 1 wherein the prosthesis further includes an ulnar component which is designed to fit against the trochlear surfaces of the humeral component, said ulnar component being in the form of a cap for fitting on the end of the ulna, the ulna having been shaped to accommodate this cap, and the cap having a concave articulating surface for sliding contact with the humeral component.

10. A prosthesis according to claim 9 wherein the ulnar component is provided with an integral fixation plate which is shaped to fit within the proximal medullary cavity of the ulna.

11. A prosthesis according to claim 9 wherein the ulnar component is provided with a pair of fixation flanges for fitting on either side of the ulna and extending from the coronoid process to the olecranon process.

12. A prosthesis according to claim 9 wherein the ulnar component is provided with a pair of fixation flanges for fitting on either side of the olecranon process and a stem for location within the coronoid process.

13. A prosthesis according to claim 9 wherein the ulnar component is provided with two spherical concave surface portions which match the first and second spherical surface portions of the humeral component.

14. A prosthesis according to claim 9 wherein the articulating surface of the ulnar component subtends an angle of about 150 degrees.

15. A prosthesis according to claim 9 wherein the humeral and ulnar components are shaped to allow for restricted lateral rotation therebetween.

16. A prosthesis according to claim 1 wherein the prosthesis further includes a radial component which is adapted to replace at least a portion of the head of the radius and has an articulating surface shaped to engage the third surface of the humeral component.

17. A prosthesis according to claim 16 wherein the radial component includes a substantially cylindrical head portion, one end of which is provided with a shallow concave spherical surface for engagement with the third surface of the humeral component and from the other side of which extends a stem member for location within the radius.

18. A prosthesis according to claim 1 wherein the humeral component is made of metal.

19. A prosthesis according to claim 1 wherein the humeral component is provided with hollows which have been machined in the interior surface and which are filled with a porous metal layer.

* * * * *